(12) United States Patent
Liu et al.

(10) Patent No.: US 11,519,879 B2
(45) Date of Patent: Dec. 6, 2022

(54) TWO METHODS OF DETERMINING PERMEABILITIES OF NATURALLY FRACTURED ROCKS FROM LABORATORY MEASUREMENTS

(71) Applicant: ARAMCO SERVICES COMPANY, Houston, TX (US)

(72) Inventors: Chao Liu, Brookshire, TX (US); Dung T. Phan, Brookshire, TX (US); Younane N. Abousleiman, Norman, OK (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 121 days.

(21) Appl. No.: 17/157,340

(22) Filed: Jan. 25, 2021

(65) Prior Publication Data
US 2022/0236226 A1    Jul. 28, 2022

(51) Int. Cl.
*G01N 33/24* (2006.01)
*G01N 29/04* (2006.01)

(52) U.S. Cl.
CPC .............. *G01N 29/04* (2013.01); *G01N 33/24* (2013.01); *G01N 2291/023* (2013.01);
(Continued)

(58) Field of Classification Search
CPC ............. G01N 29/04; G01N 2292/023; G01N 2291/0289; G01N 2291/048; G01N 2291/102
(Continued)

(56) References Cited

U.S. PATENT DOCUMENTS

| 4,964,101 | A | | 10/1990 | Liu et al. |
| 5,784,333 | A | * | 7/1998 | Tang ................ G01V 1/50 |
| | | | | 73/152.05 |

(Continued)

FOREIGN PATENT DOCUMENTS

| CA | 2159518 A1 | 3/1996 |
| CN | 103257089 A | 8/2013 |

(Continued)

OTHER PUBLICATIONS

Abousleiman et al.; "Formation Permeability Determination by Micro or Mini-Hydraulic Fracturing", Journal of Energy Resources Technology; vol. 116, Jun. 1994; pp. 104-114 (11 pages).
(Continued)

*Primary Examiner* — Jacques M Saint Surin
(74) *Attorney, Agent, or Firm* — Osha Bergman Watanabe & Burton LLP (57) ABSTRACT

A method for measuring a fracture permeability and a matrix permeability of a naturally fractured cylindrical rock sample, includes sealing both flat ends of the cylindrical sample; immersing the naturally fractured cylindrical rock sample in a fluid, and attaching an axial and a radial strain sensor to the curved surface of the sample. Furthermore, the method includes attaching a signal generator to one flat end of sample, and a signal receiver to the other flat end of the sample, and generating a harmonic excitation using the signal generator at a plurality of frequencies and recording the excitation at each of the plurality of frequencies. The method includes calculating an elastic wave propagation attribute at each of the plurality of frequencies, and inverting the elastic wave propagation attribute at each of the plurality of frequencies to determine the fracture permeability and the matrix permeability of the naturally fractured cylindrical rock sample.

15 Claims, 7 Drawing Sheets

(52) U.S. Cl.
CPC ............... *G01N 2291/0289* (2013.01); *G01N 2291/048* (2013.01); *G01N 2291/102* (2013.01)

(58) Field of Classification Search
USPC .......................................................... 73/596
See application file for complete search history.

(56) References Cited

U.S. PATENT DOCUMENTS

| | | | |
|---|---|---|---|
| 6,289,284 | B1 | 9/2001 | Yamamoto |
| 6,327,538 | B1 | 12/2001 | Chin |
| 10,662,761 | B2* | 5/2020 | Ameen ................ E21B 43/11 |
| 11,125,671 | B2* | 9/2021 | Santagati ........... G01N 15/0826 |
| 2015/0168286 | A1 | 6/2015 | Mikhailov et al. |
| 2019/0353575 | A1* | 11/2019 | Clarkson ............ G01N 15/0826 |
| 2020/0386664 | A1* | 12/2020 | Zhang ..................... G01N 7/10 |

FOREIGN PATENT DOCUMENTS

| | | |
|---|---|---|
| CN | 110261282 A | 9/2019 |
| CN | 110295885 A | 10/2019 |
| EP | 3 466 384 A2 | 1/1992 |
| GB | 2 293 653 A | 4/1996 |
| JP | 2013044536 A | 3/2013 |
| WO | 2007001746 A1 | 1/2007 |
| WO | 2019156912 A1 | 8/2019 |

OTHER PUBLICATIONS

Chen, C. et al., "A Multiply-Fractured Horizontal Well in a Rectangular Drainage Region", SPE Journal; vol. 2; Dec. 1997; pp. 455-465 (11 pages).

Chen, H. et al., "Pressure pulse-decay tests in a dual-continuum medium: An improved technique to estimate flow parameters", Journal of Natural Gas Science and Engineering; vol. 65; Feb. 10, 2019; pp. 16-24 (9 pages).

Nolte, Kenneth G., "Determination of Fracture Parameters From Fracturing Pressure Decline", SPE 8341, Society of Petroleum Engineers, Sep. 1979 (16 pages).

Galvin, Robert et al., "A simple approximation for seismic attenuation and dispersion in a fluid-saturated porous rock with aligned fractures", SEG/San Antonio 2007 Annual Meeting, DOI: 10.1190/1.2792817, pp. 1679-1683 (5 pages).

Ivan Dalen, Karel, "Multi-component acoustic characterization of porous media", Thesis, Uitgeverij BOX Press, Mar. 2011 (174 pages).

Lakshmivarahan, S. and J.M. Lewis, "Forward Sensitivity Approach to Dynamic Data Assimilation", Advances in Meteorology, Hindawi Publishing Company, 2010, pp. 1-12 (12 pages).

Liu, Chao et al., "Poroelastic Dual-Porosity/Dual-Permeability After-Closure Pressure-Curves Analysis in Hydraulic Fracturing", SPE 181748, SPE Journal, Society of Petroleum Engineers, 2016, pp. 1-21 (21 pages).

Müller, Tobias M. et al., "Seismic wave attenuation and dispersion resulting from wave-induced flow in porous rocks—A review", Geophysics, Society of Exploration Geophysicists, vol. 75, No. 5, Sep.-Oct. 2010, pp. 75A147-75A164 (18 pages).

Berryman, J.G. and H.F. Wang, "Elastic Wave Propagation and Attenuation in a Double-Porosity Dual-Permeability Medium", UCRL-JC-132xxx, Lawrence Livermore National Laboratory, Oct. 1998, pp. 1-24 (27 pages).

International Search Report and Written Opinion of the International Searching Authority issued in corresponding International Application No. PCT/US2022/013643, dated May 9, 2022 (18 pages).

Nguyen, Vinh Xuan, "Dual-Porosity and Dual-Permeability Poromechanics Solutions for Problems in Laboratory and Field Applications"; A dissertation submitted to the graduate faculty in partial fulfillment of the requirements for the degree of Doctor of Philosophy; The University of Oklahoma Graduate College; pp. iv-277; 2010 (297 pages).

Liu, Chao, "Dual-Porosity Dual-Permeability Poroelastodynamics Analytical Solutions for Mandel's Problem"; Journal of Applied Mechanics; vol. 88, Issue 1, Article 011002; pp. 011002-1-011002-10; Jan. 2021 (10 pages).

\* cited by examiner

TWO METHODS OF DETERMINING PERMEABILITIES OF NATURALLY FRACTURED ROCKS FROM LABORATORY MEASUREMENTS

BACKGROUND

Permeability is a measure of the ease with which a fluid may flow through a solid material. Fluid flows easily through materials with high permeability, and with difficulty through materials with low permeability. In the oil and gas industry, it may be frequently important to know the permeability of a rock forming a hydrocarbon reservoir to determine how easily the oil or gas will flow out of the reservoir rock and into the borehole.

It is often desirable to determine the rock matrix permeability and the fracture permeability of a core sample taken from a borehole penetrating a reservoir. These data may be used for a variety of purposes including, without limitation, reservoir simulation, planning hydraulic fracturing operations, designing drilling-mud weight schedules, and the planning the location and trajectory of future wells. For all these applications it may be desirable to measure the rock matrix permeability the fracture permeability using the same core sample.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a method for measuring a fracture permeability and a matrix permeability of a naturally fractured cylindrical rock sample, including sealing both flat ends of the cylindrical sample; immersing the naturally fractured cylindrical rock sample in a fluid, and attaching an axial and a radial strain sensor to the curved surface of the sample. Furthermore, the method includes attaching a signal generator to one flat end of sample, and a signal receiver to the other flat end of the sample, and generating a harmonic excitation using the signal generator at a plurality of frequencies and recording the excitation at each of the plurality of frequencies. The method includes calculating an elastic wave propagation attribute at each of the plurality of frequencies, and inverting the elastic wave propagation attribute at each of the plurality of frequencies to determine the fracture permeability and the matrix permeability of the naturally fractured cylindrical rock sample.

In general, in one aspect, embodiments relate to a non-transitory computer readable medium storing instructions executable by a computer processor, the instructions with functionality for generating a harmonic excitation using the signal generator and recording the harmonic excitation using the signal receiver at a plurality of frequencies. Furthermore, the instructions have functionality for calculating an elastic wave propagation attribute for the plurality of frequencies, and inverting the elastic wave propagation attribute for the plurality of frequencies to determine the fracture permeability and the matrix permeability of the naturally fractured cylindrical rock sample.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Figure 1:
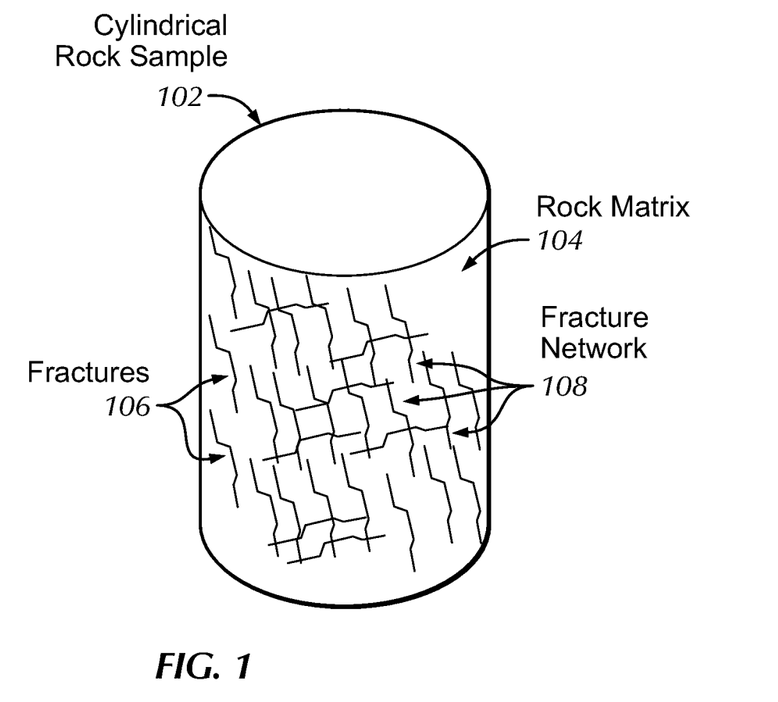
FIG. 1 an example of a naturally fractured cylindrical rock sample, in accordance with to one or more embodiments.

FIG. 1 shows a naturally fractured cylindrical rock sample (102), in accordance with one or more embodiments. Naturally fractured cylindrical rock samples (102) may be a two or three inches in diameter, and two or three inches in length. The naturally fractured cylindrical rock sample (102) may comprise a rock matrix (104), containing grains of rock, which may be connected to each other with a mineral cement, and a distribution of pores between the grains of rocks. Furthermore, the naturally fractured cylindrical rock sample (102) may contain one or more fractures (106), that may be connected together to form a fracture network (108).

The permeability of the naturally fractured cylindrical rock sample (102) may be measured and the resulting permeability values may be considered to be representative of the permeability of the hydrocarbon reservoir at the location where the naturally fractured cylindrical rock sample (102) was acquired. The permeability of the naturally fractured cylindrical rock sample (102) may result from a combination of the permeability of the rock matrix (104) and the permeability of the fracture network (108) within the naturally fractured cylindrical rock sample (102).

Figure 2:
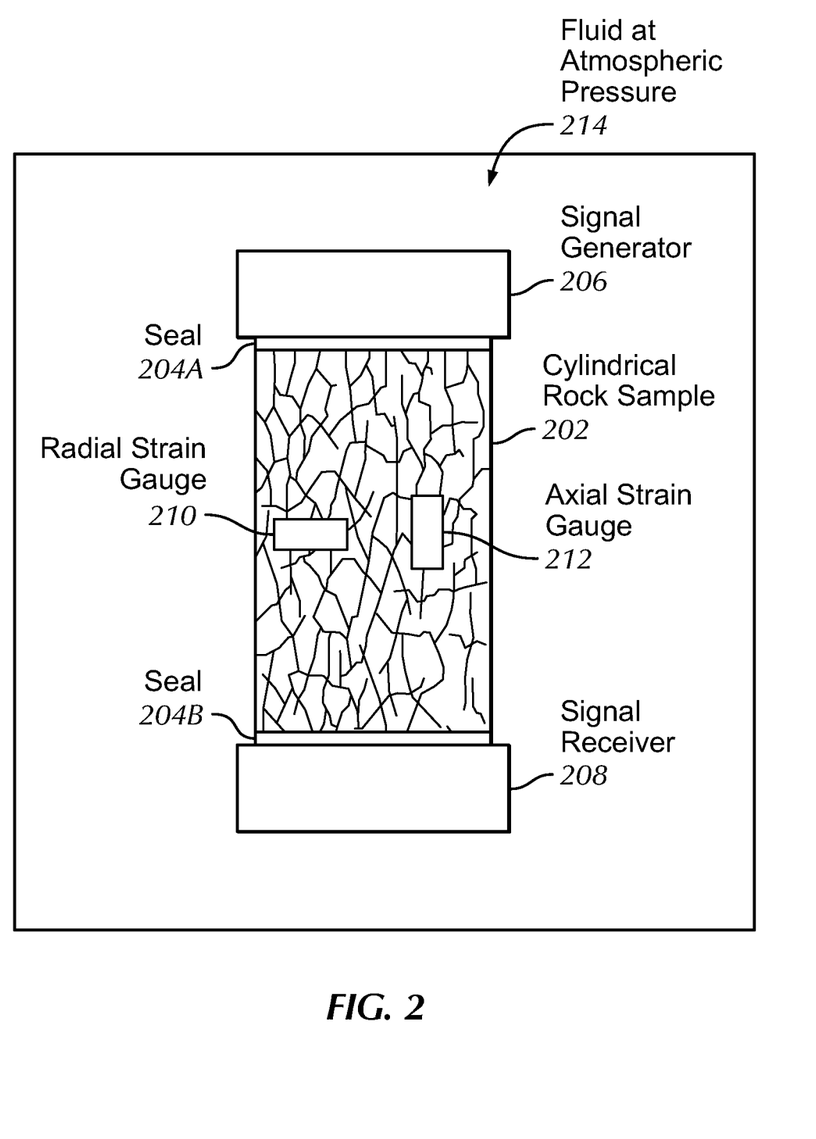
FIG. 2 an apparatus, in accordance with to one or more embodiments.

FIG. 3 shows an embodiment of an apparatus, in accordance with one or more embodiments. It comprises a naturally fractured cylindrical rock sample (202) with a seal (204A) applied to a first flat end of the naturally fractured cylindrical rock sample (202) to hydraulically seal the first flat end, and a seal (204B) applied to a second flat end of the naturally fractured cylindrical rock sample (202) to hydraulically seal the second flat end. FIG. 3 further shows a signal generator (206) attached to the seal on the first flat end, and a signal receiver (208) attached to the seal at the second flat end. In addition, FIG. 3 further shows a radial strain gauge (210) and an axial strain gauge (212) attached to the curved surface of the naturally fractured cylindrical rock sample (202). The naturally fractured cylindrical rock sample (202), the seals (204A, 204B), the signal generator (206), the signal receiver (208), the radial strain gauge (210), and the axial strain gauge (212) may all be submerged in a fluid (214). The fluid may be at atmospheric pressure.

The signal generator (206) may generate, in accordance with one or more embodiments, compressional waves in the naturally fractured cylindrical rock sample (202) which may be detected and recorded by the signal receiver (208), by the radial strain gauge (210), and by the axial strain gauge (212). The signal generator (206) may further generate, in accordance with one or more embodiments, a shear wave in the naturally fractured cylindrical rock sample (202) which may be detected and recorded by the signal receiver (208), by the radial strain gauge (210), and by the axial strain gauge (212).

In accordance with one or more embodiments, the signal generator (206) may excite, and the signal receiver (208) may detect, compressional and shear wave signals over a range of frequencies. In some embodiments, the range of frequencies may include frequencies between 10 Hertz and 10 mega-Hertz. In other embodiments, the range of frequencies may include frequencies below 10 Hertz. In still other embodiments, the range of frequencies may include frequencies above 10 mega-Hertz.

In one or more embodiments, the signal generator (206) may sequentially generate a signal at a plurality of sample frequencies, and the signal receiver (208) may detect and record the signal at a plurality of sample frequencies. In some embodiments, the signal at a sample frequency may comprise of a narrow bandwidths of frequencies close to the sample frequency. In some embodiments, the narrow bandwidth of frequencies may include frequencies above and frequencies below the sample frequency.

In some embodiments, the signal generator (206) may and the signal receiver (208) may detect and record a signal consisting of a short time duration pulse. The signal detected by the signal receiver (208) may be transformed from a recording in the time-domain into a recording in the frequency-domain, by a computer processor, using a Fourier transform. In other embodiments, the transformation of the recorded signal from the time-domain to the frequency-domain may also be performed using, without limitation, a Laplace transform, a two-sided Laplace transform, a Mellin transform, a sine and cosine transform, a Hartley transform, a short-time Fourier transform, a Chirplet transform, a Fractional Fourier transform, and a Hankel transform.

According to one or more embodiments, the velocity of the compressional waves and the velocity of the two orthogonal shear waves excited by the signal generator (206) and detected by the signal receiver (208) may be determined. Furthermore, the velocity of the compressional waves and the velocity of the shear wave may be determined at each of a plurality of frequencies. According to some embodiments, the velocity of the compressional waves and the velocity of the shear wave may be determined by comparing the time at which they were detected by the signal receiver (208) with the time at which they were excited by the signal generator (206). Alternatively, according to other embodiments, the velocity of the compressional waves and the velocity of the shear wave may be determined by comparing the phase of the signal detected by the signal receiver (208) with the phase of the signal generated by the signal generator (206).

In addition, according to one or more embodiments, the attenuation of the compressional waves, and the attenuation of the two orthogonal shear waves excited by the signal generator (206) and detected by the signal receiver (208) may be determined. The attenuation of the compressional waves may be determined by comparing the amplitude of the signal detected by the signal receiver (208) with the amplitude of the signal excited by the signal generator (206). The attenuation of the shear wave may be determined by comparing the amplitude of the signal detected by the signal receiver (208) with the amplitude of the signal excited by the signal generator (206).

In addition, according to one or more embodiments, the radial strain and axial strain may be detected over a range of frequencies generated by the signal generator (206). The radial strain may be detected by the radial strain gauge (210) and the axial strain gauge (212) may be detected by the axial strain gauge.

The compressional waves velocity, the shear waves velocity, the axial strain, and the radial strain for a naturally fractured cylindrical rock sample (102) comprising a rock matrix (104) and a network of fractures (108) may be predicted using a dual-porosity, dual permeability poroelastodynamics theory. The governing equations of the dual-porosity, dual permeability poroelastodynamics theory may be expressed as:

$$(\lambda + G - \bar{\alpha}_1 a_{11} - \bar{\alpha}_2 a_{21})\nabla(\nabla \cdot u)G\nabla^2 u - \quad \text{Equation (1)}$$
$$(\bar{\alpha}_1 a_{12} + \bar{\alpha}_2 a_{22})\nabla(\nabla \cdot w_1) - (\bar{\alpha}_1 a_{13} + \bar{\alpha}_2 a_{23})\nabla(\nabla \cdot w_2) +$$
$$\omega^2 \rho u + \omega^2 \rho_f w_1 + \omega^2 \rho_f w_2 = 0,$$

$$a_{11}\nabla(\nabla \cdot u) + a_{12}\nabla(\nabla \cdot w_1) + a_{13}\nabla(\nabla \cdot w_2) = \quad \text{Equation (2)}$$
$$\omega^2 \rho_f u + \left(\omega^2 \frac{\tau_1 \rho_f}{v_1 \phi_1} + \frac{i\omega}{\kappa_{11}}\right)w_1 + \omega^2 \frac{\rho_{23}}{v_1 v_2 \phi_1 \phi_2}w_2,$$

and:

$$a_{21}\nabla(\nabla \cdot u) + a_{22}\nabla(\nabla \cdot w_1) + a_{23}\nabla(\nabla \cdot w_2) = \quad \text{Equation (3)}$$
$$\omega^2 \rho_f u + \omega^2 \frac{\rho_{23}}{v_1 v_2 \phi_1 \phi_2}w_1 + \left(\omega^2 \frac{\tau_2 \rho_f}{v_2 \phi_2} + \frac{i\omega}{\kappa_{22}}\right)w_2,$$

where $\lambda$ and $G$ are Lamé parameters; $a_{ij}$ are related to the stiffness coefficients; $\bar{\alpha}_1$ and $\bar{\alpha}_2$ are the effective Biot's coefficients for the rock matrix and the natural fractures. u, $w_1$, and $w_2$ are the displacement vectors of the solid matrix, the fluid in rock matrix, and the fluid in the natural fractures; $\omega$ is the frequency; $\rho_f$ is the fluid density; $\tau_1$ and $\tau_2$ are the tortuosities of the rock matrix and the natural fractures; $v_1$ and $v_2$ are the volume fractions of rock matrix and natural fractures. $\phi_1$ and $\phi_2$ are the porosities of the rock matrix and the natural fractures; $\kappa_{11}$ and $\kappa_{22}$ are the mobilities of rock matrix and natural fractures.

Equation (1), equation (2), and equation (3) form a coupled set of equations which may be solved analytically to give velocities for three compressional waves, $v_{pk}$, k=1, 2, 3, and one shear wave, $v_s$:

$$v_s = \sqrt{\frac{G}{\rho + \frac{2b_{12} - b_{11} - b_{22}}{b_{11}b_{22} - b_{12}^2}\rho_f^2}} \quad \text{Equation (4)}$$

$$v_{pk} = \sqrt{\frac{\omega^2}{-Y_k}} \quad k = 1, 2, 3 \quad \text{Equation (5)}$$

where $$Y_1 = -\frac{A_4}{3A_6} + \frac{(1+\sqrt{3}\,i)(-A_4^2 + 3A_2A_6)}{3^3\sqrt[3]{4}\,A_6\varphi_1} - \frac{(1-\sqrt{3}\,i)X_1}{6\sqrt[3]{2}\,A_6} \quad \text{Equation (6)}$$

$$Y_2 = -\frac{A_4}{3A_6} - \frac{\sqrt[3]{2}\,(-A_4^2 + 3A_2A_6)}{3A_6\varphi_1} + \frac{X_1}{3\sqrt[3]{2}\,A_6} \quad \text{Equation (7)}$$

$$Y_3 = -\frac{A_4}{3A_6} + \frac{(1-\sqrt{3}\,i)(-A_4^2 + 3A_2A_6)}{3^3\sqrt[3]{4}\,A_6\varphi_1} - \frac{(1+\sqrt{3}\,i)X_1}{6\sqrt[3]{2}\,A_6} \quad \text{Equation (8)}$$

$$X_1 = \sqrt[3]{-2A_4^3 + 9A_2A_4A_6 - 27A_0A_6^2 + \sqrt{4(-A_4^2 + 3A_2A_6)^3 + (-2A_4^3 + 9A_2A_4A_6 - 27A_0A_6^2)^2}} \quad \text{Equation (9)}$$

and the parameters $b_{11}$, $b_{12}$, $b_{22}$, $A_2$, $A_4$, and $A_6$ are determined by the coefficients in equations (1), (2) and (3).

Similarly, an analytical solution for the radial strain may be written as:

$$\varepsilon_r = \sum_{m=1}^{\infty} i\frac{m\pi}{H} B_1 \sqrt{\delta_s}\left(e^{\sqrt{\delta_s}r} + e^{-\sqrt{\delta_s}r}\right)\left(e^{i\frac{m\pi}{H}z} + e^{-i\frac{m\pi}{H}z}\right) + \quad \text{Equation (10)}$$

$$\sum_{m=1}^{\infty}\sum_{j=1}^{3} \delta_{pj} C_{1j}\left(e^{\sqrt{\delta_{pj}}r} + e^{-\sqrt{\delta_{pj}}r}\right)\left(e^{i\frac{m\pi}{H}z} + e^{-i\frac{m\pi}{H}z}\right) +$$

$$\sum_{j=1}^{3} C_{2j} il_{pj}(e^{il_{pj}r} + e^{il_{pj}r}).$$

and for the axial strain as:

$$\varepsilon_z = -\sum_{m=1}^{\infty} \sqrt{\delta_s}\, B_1 \frac{m\pi}{H}\left(e^{\sqrt{\delta_s}r} + e^{-\sqrt{\delta_s}r}\right)\left(e^{i\frac{m\pi}{H}z} + e^{-i\frac{m\pi}{H}z}\right) - \quad \text{Equation (11)}$$

$$\sum_{m=1}^{\infty}\sum_{j=1}^{3} \frac{m^2\pi^2}{H^2} C_{1j}\left(e^{\sqrt{\delta_{pj}}r} + e^{-\sqrt{\delta_{pj}}r}\right)$$

$$\left(e^{i\frac{m\pi}{H}z} + e^{-i\frac{m\pi}{H}z}\right) + \sum_{j=1}^{3} C_{3j} il_{pj}(e^{il_{pj}z} + e^{-il_{pj}z}).$$

Figure 3A:
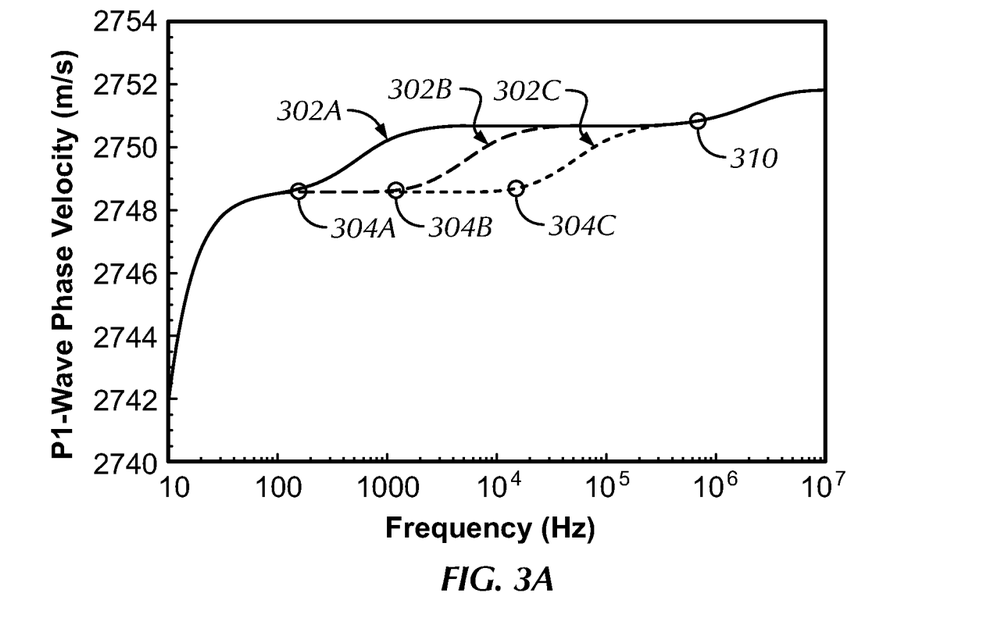
FIG. 3A an example of the first compressional wave velocities in accordance with to one or more embodiments.

FIG. 3A shows three examples of the first compressional wave velocity, $v_{p1}$, modeled using equation (5), in accordance with one or more embodiments, for a range of frequencies (302A, 302B, 302C). All of the velocity versus frequency curves (302A, 302B, 302C) correspond to a model with the parameters given in Table 1:

TABLE 1

| Parameters | K (GPa) | α | B | k (mD) | V (%) | φ | τ |
|---|---|---|---|---|---|---|---|
| Rock Matrix | 10 | 0.8 | 0.6 | 5.6 | 98.2 | 0.178 | 3.3 |
| Fractures | 0.26 | 1.0 | 0.9 | $k_f$ | 1.8 | 1.0 | 1.0 |

The first velocity versus frequency curve, (302A), may be determined using the dual-porosity, dual-permeability poroelastodynamics theory and a value of fracture permeability, $k_f$=5600 millidarcy. The second velocity versus frequency curve, (302B), may be determined using the dual-porosity, dual-permeability poroelastodynamic theory and a value of fracture permeability, $k_f$=560 millidarcy, and the third velocity versus frequency curve, (302C), may be determined using the dual-porosity, dual-permeability poroelastodynamics theory and a value of fracture permeability, $k_f$=56 millidarcy.

Figure 3B:
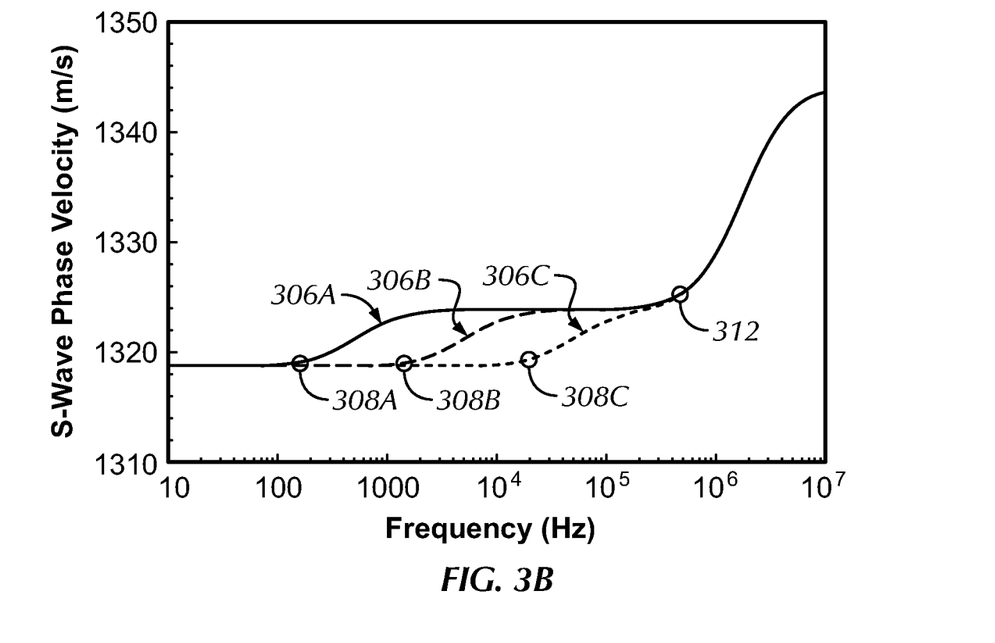
FIG. 3B an example of shear wave velocities in accordance with to one or more embodiments.

FIG. 3B shows three examples of the shear wave velocity, $v_s$, modeled using equation (4), in accordance with one or more embodiments, for a range of frequencies (306A, 306B, 306C). All of the velocity versus frequency curves (306A, 306B, 306C) correspond to a model with the parameters given in Table 1. The first shear wave velocity versus frequency curve, (306A), may be determined using the dual-porosity, dual-permeability poroelastodynamics theory and a value of fracture permeability, $k_f$=5600 millidarcy. The second shear wave velocity versus frequency curve, (306B), may be determined using the dual-porosity, dual-permeability poroelastodynamics theory and a value of fracture permeability, $k_f$=560 millidarcy, and the third shear wave velocity versus frequency curve, (306C), may be determined using the dual-porosity, dual-permeability poroelastodynamics theory and a value of fracture permeability, $k_f$=56 millidarcy.

Figure 4A:
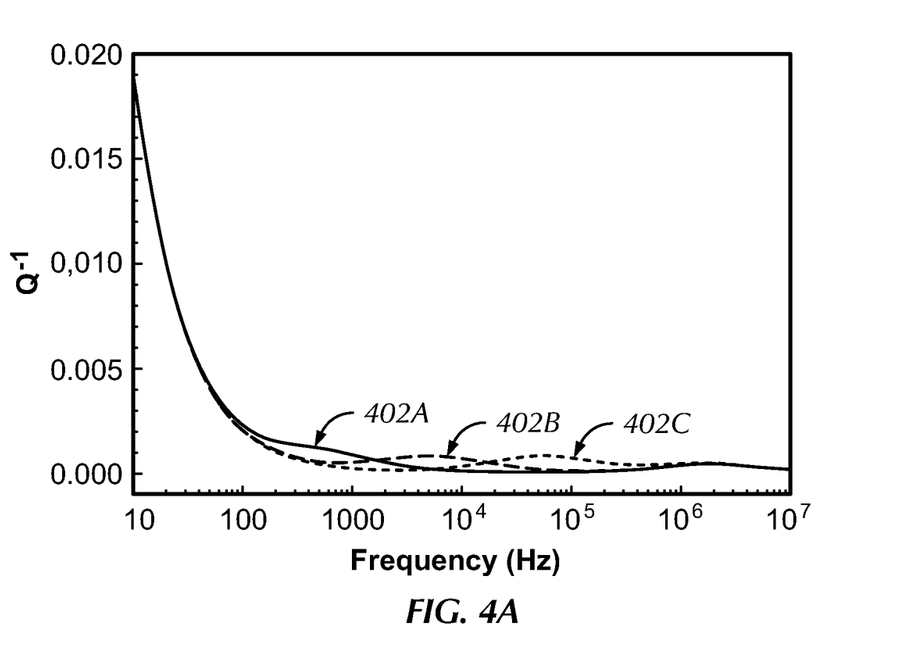
FIG. 4A an example of the first compressional wave attenuations, in accordance with to one or more embodiments.

FIG. 4A shows three examples of the first compressional wave attenuation, modeled using equation (5), in accordance with one or more embodiments, for a range of frequencies (402A, 402B, 402C). All of the attenuation versus frequency curves (402A, 402B, 402C) correspond to a model with the parameters given in Table 1. The first attenuation versus frequency curve, (402A), may be determined using the dual-porosity, dual-permeability poroelastodynamics theory and a value of fracture permeability, $k_f$=5600 millidarcy. The second attenuation versus frequency curve, (402B), may be determined using the dual-porosity, dual-permeability poroelastodynamics theory and a value of fracture permeability, $k_f$=560 millidarcy, and the third attenuation versus frequency curve, (402C), may be determined using the dual-porosity, dual-permeability poroelastodynamics theory and a value of fracture permeability, $k_f$=56 millidarcy.

Figure 4B:
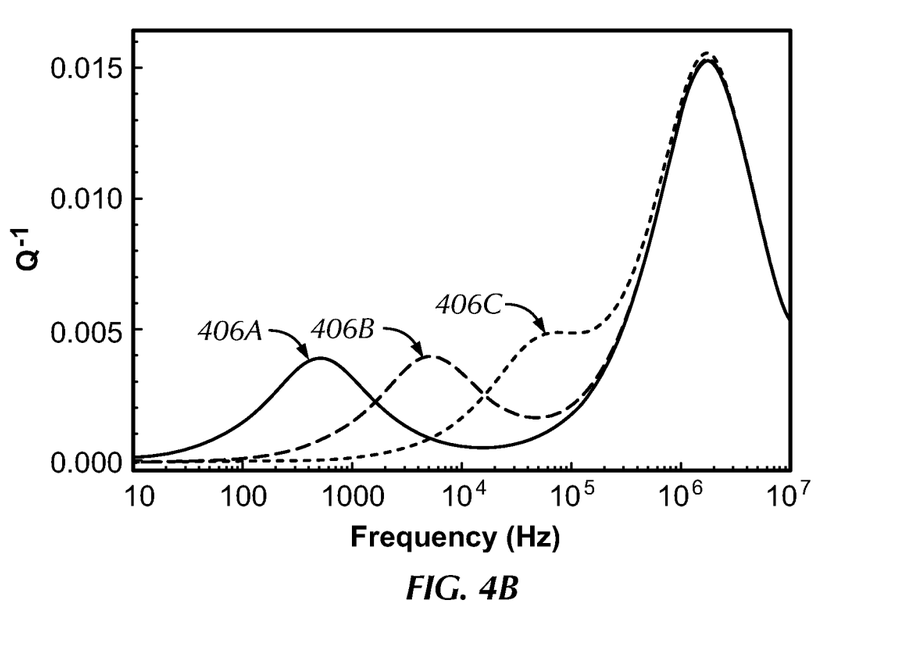
FIG. 4B an example of shear wave attenuations, in accordance with to one or more embodiments.

FIG. 4B shows three examples of the shear wave attenuation modeled using equation (4), in accordance with one or more embodiments, for a range of frequencies (406A, 406B, 406C). All of the attenuation versus frequency curves (406A, 406B, 406C) correspond to a model with the parameters given in Table 1. The first shear wave attenuation versus frequency curve, (406A), may be determined using the dual-porosity, dual-permeability poroelastodynamics theory and a value of fracture permeability, $k_f$=5600 millidarcy. The second shear wave attenuation versus frequency curve, (406B), may be determined using the dual-porosity, dual-permeability poroelastodynamics theory and a value of fracture permeability, $k_f$=560 millidarcy, and the third shear wave attenuation versus frequency curve, (406C), may be determined using the dual-porosity, dual-permeability poroelastodynamics theory and a value of fracture permeability, $k_f$=56 millidarcy.

Figure 5A:
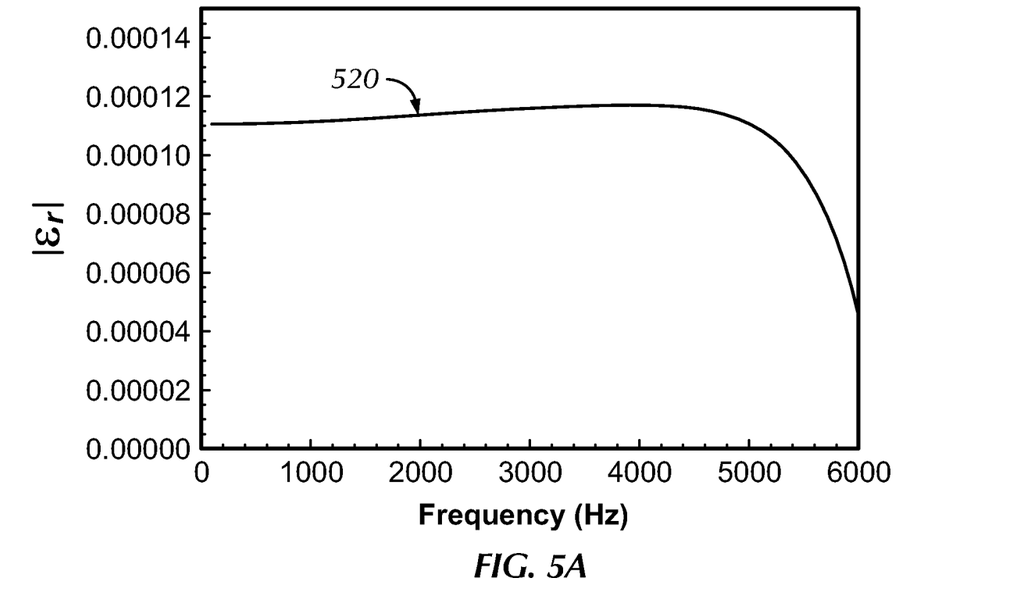
FIG. 5A an example of radial strain, in accordance with to one or more embodiments.
Figure 5B:
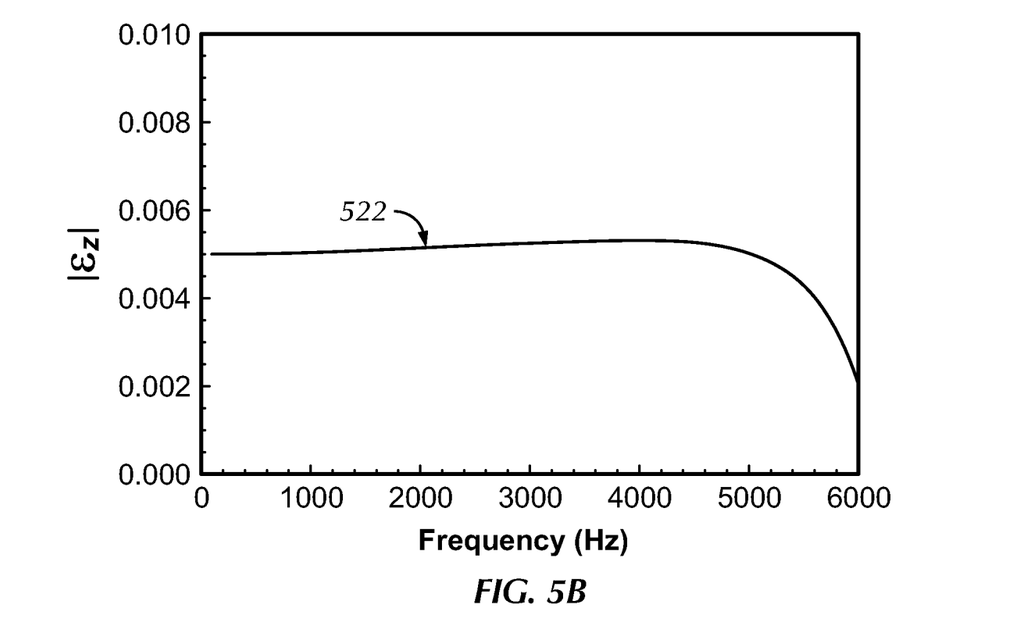
FIG. 5B an example of axial strain, in accordance with to one or more embodiments.

FIG. 5A shows the radial strain modeled using equation (10), in accordance with one or more embodiments, generated by the signal generator (206) for a range of frequencies (520). FIG. 5B shows the axial strain modeled using equation (11), in accordance with one or more embodiments, generated by the signal generator (206) for a range of frequencies (522).

In accordance with one or more embodiments, the permeability of the fracture network may be determine based, at least in part, upon a first characteristic frequency, $\omega_{c1}$, of the compressional wave velocity, and the shear wave velocity. The first characteristic frequency, $\omega_{c1}$, is the lowest frequency at which the shear wave velocity, and the compressional wave velocity have an inflection point (304A, 304B, 304C)

In accordance with one or more embodiments, the permeability of the rock matrix may be determine based, at least in part, upon a second characteristic frequency, $\omega_{c2}$, of the compressional wave velocity, and the shear wave velocity. The second characteristic frequency, $\omega_{c2}$, is the higher frequency at which the shear wave velocity curve has an inflection point (312), and the compressional wave velocity curve has an inflection point (310).

In accordance with one or more embodiments, the fracture network permeability may be found from the first characteristic frequency, $\omega_{c1}$, using an analytical solution that may be written as:

$$k_f = \frac{0.01\mu\phi}{\omega_{c1}\rho} \qquad \text{Equation (12)}$$

In accordance with one or more embodiments, the rock matrix permeability may be found from the first characteristic frequency, $\omega_{c2}$, using an analytical solution that may be written as:

$$k_m = \frac{0.01\mu\phi}{\omega_{c2}\rho} \qquad \text{Equation (13)}$$

where $k_f$ is the fracture network permeability, and $k_m$ is the rock matrix permeability.

In accordance with still further embodiments, one or more laboratory measurement may be simulated using a dual-porosity, dual permeability poroelastodynamics theory. In accordance with one or more embodiments, the signals recorded by the signal receiver (208) may be simulated by solving equations (1), (2), and (3). In accordance with one or more embodiments, the signals recorded by the radial strain gauge (210) may be simulated by solving equation (10). In accordance with one or more embodiments, the signals recorded by the axial strain gauge (212) may be simulated by solving equation (11).

In accordance with one or more embodiments, the rock matrix permeability, and the fracture network permeability may be adjusted to cause the simulated measurements obtained using a dual-porosity, dual permeability poroelastodynamics theory to match the one or more laboratory measurements. The values of the rock matrix permeability, and the fracture network permeability, which cause the simulation measurements to best match the one or more laboratory measurements may then be determined to be the true rock matrix permeability, and the true fracture network permeability of the naturally fractured cylindrical rock sample (202).

In accordance with one or more embodiments, a cost function may be defined as the weighted sum of the square of the difference between the simulated measurements and the laboratory measurements. The true rock matrix permeability, and the true fracture network permeability, may then be determined by minimizing the cost function. The minimization of the cost function may be performed using data assimilation technique, such as the forward sensitivity method. In other embodiments, the minimization of the cost function may be performed using a steepest-descent method, or a Monte-Carlo search method. One of ordinary skill in the art will appreciate there are a plurality of other methods for minimizing the cost function.

Figure 6:
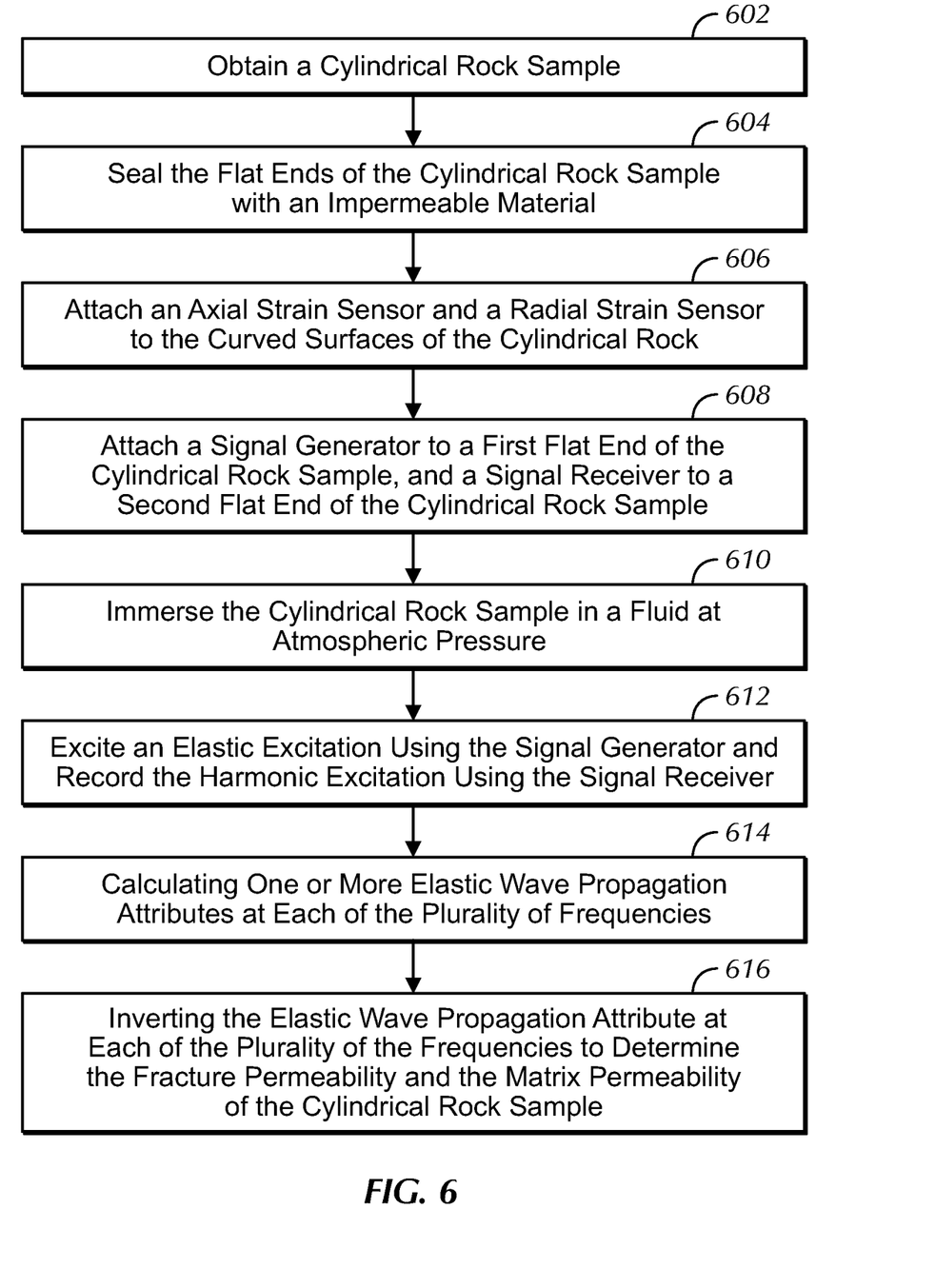
FIG. 6 a flowchart, in accordance with to one or more embodiments.

FIG. 6 shows a flowchart in accordance with one or more embodiments. In Block 602 a naturally fractured cylindrical rock sample (102) may be obtained. The naturally fractured cylindrical rock sample (102) may contain a rock matrix (104) with a rock matrix permeability and a fracture network (108) with a fracture network permeability.

In Block 604, in accordance with one or more embodiments, the flat ends of the naturally fractured cylindrical rock sample (202) may be sealed (204A, 204B) with an impermeable material.

In Block 606, in accordance with one or more embodiments, an axial strain sensor (212) and a radial strain sensor (210) may be attached to the curved surfaces of the naturally fractured cylindrical rock sample (202).

In Block 608, in accordance with one or more embodiments, a signal generator (206) may be attached to a first flat end of the naturally fractured cylindrical rock sample (202), and a signal receiver (208) may be attached to a second flat end of the naturally fractured cylindrical rock sample (202).

In accordance with one or more embodiments, in Block 610 the naturally fractured cylindrical rock sample (202) may be immersed in a fluid at atmospheric pressure (214).

In Block 612 an elastic excitation may be excited using the signal generator and record the harmonic excitation using the signal receiver, according to one or more embodiments.

In Block 614, according to one or more embodiments, one or more elastic wave propagation attributes at each of the plurality of frequencies may be calculated. These attributes may include a compressional wave velocity (302A, 302B, 302C), a shear wave velocity (306A, 306B, 306C), a compressional wave attenuation (402A, 402B, 402C), a shear wave attenuation (406A, 406B, 406C), a radial strain (520), an axial strain (522) and elastic waveforms recorded by the signal receiver (208).

In accordance with some embodiments, in Block 416 the elastic wave propagation attributes at each of the plurality of frequencies may be inverted to determine the fracture network permeability and the rock matrix permeability of the naturally fractured cylindrical rock sample (202). In accordance with one or more embodiments, the inversion of the elastic wave propagation attributes may be performed by determining a first characteristic frequency, and a second characteristic frequency, and determining a fracture matrix permeability from the first characteristic frequency, and a rock matrix permeability from the second characteristic frequency. In accordance with one or more embodiments, the inversion may be performed by simulating the elastic attributes based, at least in part, on a dual-porosity, dual-permeability poroelastodynamics theory, and minimizing a cost function formed from the difference between the simulated measurements and the laboratory measurements of the elastic attributes.

Figure 7:
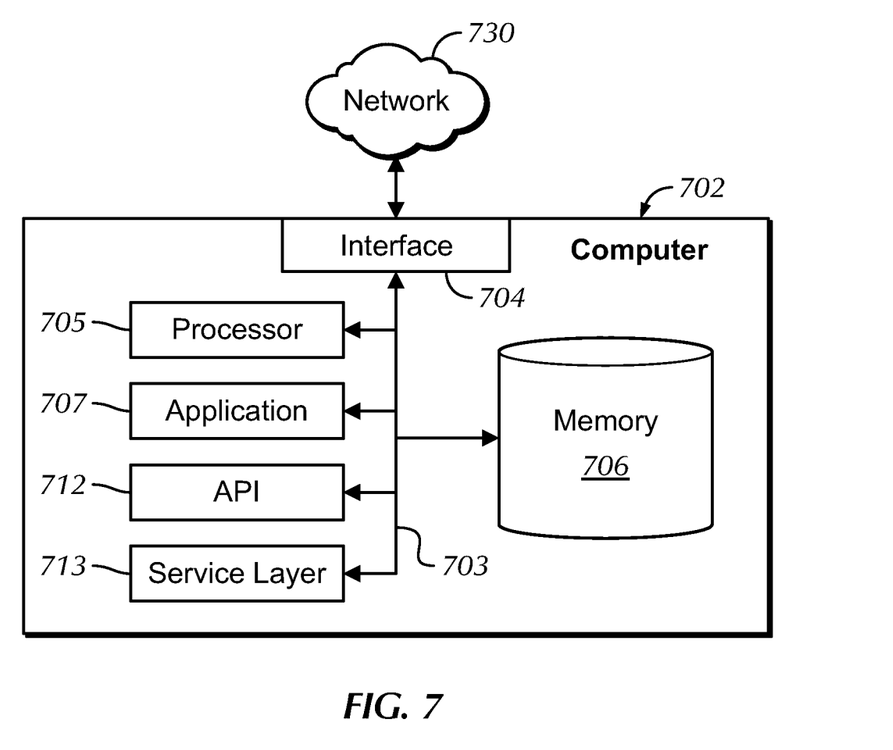
FIG. 7 an example of a computer system, according to one or more embodiments.

Embodiments may be implemented on a computer system. FIG. 7 is a block diagram of a computer system (702) used to provide computational functionalities associated with described algorithms, methods, functions, processes, flows, and procedures as described in the instant disclosure, according to an implementation. The illustrated computer (702) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (702) may include a computer that includes an input device, such as a keypad, keyboard, touch screen, or other device that can accept user information, and an output device that conveys information associated with the operation of the computer (702), including digital data, visual, or audio information (or a combination of information), or a GUI.

The computer (702) can serve in a role as a client, network component, a server, a database or other persistency, or any other component (or a combination of roles) of a computer system for performing the subject matter described in the instant disclosure. The illustrated computer (702) is communicably coupled with a network (730). In some implementations, one or more components of the computer (702) may be configured to operate within environments, including cloud-computing-based, local, global, or other environment (or a combination of environments).

At a high level, the computer (702) is an electronic computing device operable to receive, transmit, process, store, or manage data and information associated with the described subject matter. According to some implementations, the computer (702) may also include or be communicably coupled with an application server, e-mail server, web server, caching server, streaming data server, business intelligence (BI) server, or other server (or a combination of servers).

The computer (702) can receive requests over network (730) from a client application (for example, executing on another computer (702)) and responding to the received requests by processing the said requests in an appropriate software application. In addition, requests may also be sent to the computer (702) from internal users (for example, from a command console or by other appropriate access method), external or third-parties, other automated applications, as well as any other appropriate entities, individuals, systems, or computers.

Each of the components of the computer (702) can communicate using a system bus (703). In some implementations, any or all of the components of the computer (702), both hardware or software (or a combination of hardware and software), may interface with each other or the interface (704) (or a combination of both) over the system bus (703) using an application programming interface (API) (712) or a service layer (713) (or a combination of the API (712) and service layer (713). The API (712) may include specifications for routines, data structures, and object classes. The API (712) may be either computer-language independent or dependent and refer to a complete interface, a single function, or even a set of APIs. The service layer (713) provides software services to the computer (702) or other components (whether or not illustrated) that are communicably coupled to the computer (702). The functionality of the computer (702) may be accessible for all service consumers using this service layer. Software services, such as those provided by the service layer (713), provide reusable, defined business functionalities through a defined interface. For example, the interface may be software written in JAVA, C++, or other suitable language providing data in extensible markup language (XML) format or other suitable format. While illustrated as an integrated component of the computer (702), alternative implementations may illustrate the API (712) or the service layer (713) as stand-alone components in relation to other components of the computer (702) or other components (whether or not illustrated) that are communicably coupled to the computer (702). Moreover, any or all parts of the API (712) or the service layer (713) may be implemented as child or sub-modules of another software module, enterprise application, or hardware module without departing from the scope of this disclosure.

The computer (702) includes an interface (704). Although illustrated as a single interface (704) in FIG. 7, two or more interfaces (704) may be used according to particular needs, desires, or particular implementations of the computer (702). The interface (704) is used by the computer (702) for communicating with other systems in a distributed environment that are connected to the network (730). Generally, the interface (704 includes logic encoded in software or hardware (or a combination of software and hardware) and operable to communicate with the network (730). More specifically, the interface (704) may include software supporting one or more communication protocols associated with communications such that the network (730) or interface's hardware is operable to communicate physical signals within and outside of the illustrated computer (702).

The computer (702) includes at least one computer processor (705). Although illustrated as a single computer processor (705) in FIG. 7, two or more processors may be used according to particular needs, desires, or particular implementations of the computer (702). Generally, the computer processor (705) executes instructions and manipulates data to perform the operations of the computer (702) and any algorithms, methods, functions, processes, flows, and procedures as described in the instant disclosure.

The computer (702) also includes a memory (706) that holds data for the computer (702) or other components (or a combination of both) that can be connected to the network (730). For example, memory (706) can be a database storing data consistent with this disclosure. Although illustrated as a single memory (706) in FIG. 7, two or more memories may be used according to particular needs, desires, or particular implementations of the computer (702) and the described functionality. While memory (706) is illustrated as an integral component of the computer (702), in alternative implementations, memory (706) can be external to the computer (702).

The application (707) is an algorithmic software engine providing functionality according to particular needs, desires, or particular implementations of the computer (702), particularly with respect to functionality described in this disclosure. For example, application (707) can serve as one or more components, modules, applications, etc. Further, although illustrated as a single application (707), the application (707) may be implemented as multiple applications (707) on the computer (702). In addition, although illustrated as integral to the computer (702), in alternative implementations, the application (707) can be external to the computer (702).

There may be any number of computers (702) associated with, or external to, a computer system containing computer (702), each computer (702) communicating over network (730). Further, the term "client," "user," and other appropriate terminology may be used interchangeably as appropriate without departing from the scope of this disclosure. Moreover, this disclosure contemplates that many users may use one computer (702), or that one user may use multiple computers (702).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed is:

1. A method for measuring a fracture permeability and a matrix permeability of a naturally fractured cylindrical rock sample, comprising:
    sealing a first flat end of the naturally fractured cylindrical rock sample;
    sealing a second flat end of the naturally fractured cylindrical rock sample;
        immersing the naturally fractured cylindrical rock sample in a fluid;
    attaching an axial strain sensor and a radial strain sensor to a curved surface of the naturally fractured cylindrical rock sample;
    attaching a signal generator to the first flat end of the naturally fractured cylindrical rock sample;
    attaching a signal receiver to the second flat end of the naturally fractured cylindrical rock sample;
    generating a harmonic excitation using the signal generator at a plurality of frequencies;
    recording, using the signal receiver, the harmonic excitation at each of the plurality of frequencies;
    calculating an elastic wave propagation attribute at each of the plurality of frequencies; and
    inverting the elastic wave propagation attribute at each of the plurality of frequencies to determine the fracture permeability and the matrix permeability of the naturally fractured cylindrical rock sample.

2. The method of claim 1,
    wherein the naturally fractured cylindrical rock sample is immersed in a fluid at atmospheric pressure.

3. The method of claim 1,
    wherein the elastic wave propagation attribute is selected from the group consisting of a first compressional wave propagation velocity, a shear wave propagation velocity, a first compressional wave attenuation, a shear wave attenuation, an axial strain, and a radial strain.

4. The method of claim 1,
    wherein the inverting the elastic wave propagation attribute, further comprises:
        determining a characteristic frequency of the naturally fractured cylindrical rock sample; and
        determining the fracture permeability and the matrix permeability of the rock based on the characteristic frequency of the naturally fractured cylindrical rock sample and a theory of dual-porosity dual-permeability poroelastodynamics.

5. The method of claim 1,
    wherein the inverting the elastic wave propagation attribute, further comprises:
        determining a value of the fracture permeability and a value of the matrix permeability of the naturally fractured cylindrical rock sample which minimizes a measure of a difference between a measured and a predicted value of the elastic wave propagation attribute, summed over a plurality of frequencies.

6. The method of claim 5,
    wherein the predicted value of the elastic wave propagation attribute is determined using the theory of dual-porosity dual-permeability poroelastodynamics.

7. The method of claim 5, further comprises:
    summing over a plurality of frequencies using a weighted-sum, wherein one or more elastic wave propagation attributes are assigned more importance than another elastic wave propagation attributes.

8. The method of claim 5,
    wherein the measure of the difference between a measured value of the elastic wave propagation attribute and a predicted value of the elastic wave propagation attribute, summed over a plurality of frequencies is the square of the differences between the measured and the predicted value summed over the plurality of frequencies.

9. A non-transitory computer readable medium storing instructions executable by a computer processor, the instructions comprising functionality for:
    generating a harmonic excitation using the signal generator and recording the harmonic excitation using the signal receiver at a plurality of frequencies;
    calculating an elastic wave propagation attribute for the plurality of frequencies; and
    inverting the elastic wave propagation attribute for the plurality of frequencies to determine the fracture permeability and the matrix permeability of the naturally fractured cylindrical rock sample.

10. The non-transitory computer readable medium of claim 9, wherein the instructions further comprise functionality for:
    selecting, the elastic wave propagation attributes from the group consisting of a first compressional wave propagation velocity, a shear wave propagation velocity, a first compressional wave attenuation, a shear wave attenuation, an axial strain, and a radial strain.

11. The non-transitory computer readable medium of claim 9, wherein the instructions further comprise functionality for:
   determining a characteristic frequency of the naturally fractured cylindrical rock sample; and
   determining the fracture permeability and the matrix permeability of the rock based, at least in part, on the characteristic frequency of the naturally fractured cylindrical rock sample and a theory of dual-porosity dual-permeability poroelastodynamics.

12. The non-transitory computer readable medium of claim 9, wherein the instructions further comprise functionality for:
   determining the value of the fracture permeability and the value of the matrix permeability of the naturally fractured cylindrical rock which minimize a measure of the difference between a measured and a predicted value of the elastic wave propagation attribute, summed over a plurality of frequencies.

13. The non-transitory computer readable medium of claim 9, wherein the instructions further comprise functionality for:
   predicting the value of the elastic wave propagation attributes based, at least in part, using a theory of dual-porosity dual-permeability poroelastodynamics.

14. The non-transitory computer readable medium of claim 9, wherein the instructions further comprise functionality for:
   summing over a plurality of frequencies using a weighted-sums wherein one or more elastic wave propagation attributes are assigned more weight than other elastic wave propagation attributes.

15. The non-transitory computer readable medium of claim 9, wherein the instructions further comprise functionality for:
   wherein, the measure of the difference between a measured value of the elastic wave propagation attribute and a predicted value of the elastic wave propagation attribute, summed over a plurality of frequencies is the square of the differences between the measured and the predicted value summed over the plurality of frequencies.

* * * * *